US005747504A

United States Patent [19]
Henning et al.

[11] Patent Number: 5,747,504
[45] Date of Patent: May 5, 1998

[54] METHOD OF TREATING CARDIAC INSUFFICIENCY USING ANGIOTENSIN-CONVERTING ENZYME INHIBITORS

[75] Inventors: Rainer Henning, Hattersheim am Main; Hansjörg Urbach, Kronberg/Taunus; Volker Teetz, Hofheim am Taunus; Rolf Geiger, Frankfurt am Main; Bernward Schölkens, Kelkheim, all of Germany

[73] Assignee: Hoechst Aktiengesellschaft, Frankfurt am Main, Germany

[21] Appl. No.: 709,286

[22] Filed: Sep. 6, 1996

Related U.S. Application Data

[60] Continuation of Ser. No. 445,543, May 22, 1995, Pat. No. 5,684,016, which is a division of Ser. No. 359,860, Dec. 20, 1994, which is a division of Ser. No. 188,745, Jan. 31, 1994, Pat. No. 5,403,856, which is a continuation of Ser. No. 920,173, Jul. 27, 1992, abandoned, which is a continuation of Ser. No. 636,001, Jan. 3, 1991, abandoned, which is a continuation of Ser. No. 313,491, Feb. 22, 1989, abandoned, which is a continuation of Ser. No. 721,705, Apr. 10, 1985, abandoned.

[30] Foreign Application Priority Data

Apr. 12, 1984 [DE] Germany .................. 34 13 710.6

[51] Int. Cl.⁶ .......................................... A61K 31/47
[52] U.S. Cl. ........................................................ 514/307
[58] Field of Search .......................................... 514/307

[56] References Cited

U.S. PATENT DOCUMENTS

| | | | |
|---|---|---|---|
| 4,344,949 | 8/1982 | Hoefle et al. | 424/258 |
| 4,350,704 | 9/1982 | Hoefle et al. | 424/274 |
| 4,374,829 | 2/1983 | Harris et al. | 424/177 |
| 4,374,847 | 2/1983 | Gruenfeld | 424/274 |
| 4,404,206 | 9/1983 | Vincent et al. | 424/258 |
| 4,425,355 | 1/1984 | Hoefle et al. | 424/274 |
| 4,442,089 | 4/1984 | Horovitz | 514/913 |
| 4,508,729 | 4/1985 | Vincent et al. | 514/419 |
| 4,515,803 | 5/1985 | Henning et al. | 514/419 |
| 4,525,301 | 6/1985 | Henning et al. | 260/112.5 |
| 4,558,064 | 12/1985 | Teetz et al. | 514/409 |
| 4,558,065 | 12/1985 | Urbach et al. | 514/412 |
| 4,562,202 | 12/1985 | Urbach et al. | 514/423 |
| 4,565,819 | 1/1986 | Vincent et al. | 514/307 |
| 4,584,285 | 4/1986 | Doll et al. | 514/19 |
| 4,584,299 | 4/1986 | Steffen et al. | 514/252 |
| 4,587,258 | 5/1986 | Gold et al. | 514/412 |
| 4,591,598 | 5/1986 | Urbach et al. | 514/412 |
| 4,614,805 | 9/1986 | Urbach et al. | 548/427 |
| 4,620,012 | 10/1986 | Henning et al. | 548/411 |
| 4,624,962 | 11/1986 | Henning et al. | 514/412 |
| 4,659,838 | 4/1987 | Lerch | 372/25 |
| 4,668,796 | 5/1987 | Geiger et al. | 548/452 |
| 4,668,797 | 5/1987 | Urbach et al. | 548/452 |
| 4,678,800 | 7/1987 | Stanton et al. | 514/412 |
| 4,684,662 | 8/1987 | Henning et al. | 548/452 |
| 4,691,022 | 9/1987 | Henning et al. | 548/408 |
| 4,714,708 | 12/1987 | Urbach et al. | 514/412 |
| 4,727,160 | 2/1988 | Teetz et al. | 548/452 |
| 4,808,573 | 2/1989 | Gold et al. | 514/19 |
| 4,818,749 | 4/1989 | Gold et al. | 514/412 |
| 4,822,894 | 4/1989 | Geiger et al. | 548/252 |
| 4,831,157 | 5/1989 | Gold et al. | 548/452 |
| 4,849,524 | 7/1989 | Henning et al. | 548/411 |
| 4,868,307 | 9/1989 | Barton et al. | 546/256 |
| 4,879,403 | 11/1989 | Teetz et al. | 560/38 |
| 4,886,827 | 12/1989 | Urbach et al. | 514/412 |
| 4,920,144 | 4/1990 | Urbach et al. | 514/412 |
| 4,933,361 | 6/1990 | Urbach et al. | 514/419 |
| 4,983,623 | 1/1991 | Henning et al. | 514/414 |
| 4,997,260 | 3/1991 | Henning et al. | 350/96 |
| 5,053,519 | 10/1991 | Teetz et al. | 548/452 |
| 5,055,483 | 10/1991 | Ruger et al. | 514/412 |
| 5,061,722 | 10/1991 | Teetz et al. | 548/452 |
| 5,098,910 | 3/1992 | Becker et al. | 514/299 |

FOREIGN PATENT DOCUMENTS

| | | |
|---|---|---|
| 0012401 | 6/1980 | European Pat. Off. . |
| 0012845 | 6/1980 | European Pat. Off. . |
| 0018549 | 11/1980 | European Pat. Off. . |
| 0037231 A2 | 10/1981 | European Pat. Off. . |
| 0046953 | 3/1982 | European Pat. Off. . |
| 0048159 | 3/1982 | European Pat. Off. . |
| 0049658 | 4/1982 | European Pat. Off. . |
| 049658 | 4/1982 | European Pat. Off. . |
| 0050800 | 5/1982 | European Pat. Off. . |
| 0050800A1 | 5/1982 | European Pat. Off. . |
| 0050850 A1 | 5/1982 | European Pat. Off. . |
| 0051301 | 5/1982 | European Pat. Off. . |
| 0052991 | 6/1982 | European Pat. Off. . |
| 0065301 | 11/1982 | European Pat. Off. . |
| 065301 | 11/1982 | European Pat. Off. . |
| 0079022 | 5/1983 | European Pat. Off. . |
| 0079521 | 5/1983 | European Pat. Off. . |
| 0080822 | 6/1983 | European Pat. Off. . |
| 0084164 | 7/1983 | European Pat. Off. . |
| 0088341 | 9/1983 | European Pat. Off. . |
| 089637 | 9/1983 | European Pat. Off. . |

(List continued on next page.)

OTHER PUBLICATIONS

Gross, Chemical Abstract 100: 151036a (1983).
Ader et al, Circulation, 61 (5) (1980), pp. 931–937.
Gavras et al, Circulation, 58 (5), (1978), pp. 770–776.

(List continued on next page.)

*Primary Examiner*—John M. Ford
*Attorney, Agent, or Firm*—Finnegan, Henderson, Farabow, Garrett & Dunner, L.L.P.

[57] ABSTRACT

The invention relates to a method of treating cardiac insufficiency by using compounds of the formula I

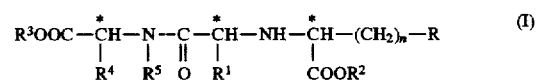

in which n is 1 or 2, R, R¹, R² and R³ are identical or different and each denote hydrogen or an organic radical and R⁴ and R⁵, together with the atoms carrying them, form a mono-, bi- or tri-cyclic heterocyclic ring system. The invention furthermore relates to compounds of the formula I and agents containing these for use in the treatment of the abovementioned disease.

3 Claims, No Drawings

FOREIGN PATENT DOCUMENTS

| | | |
|---|---|---|
| 0090362 | 10/1983 | European Pat. Off. . |
| 0115091 | 8/1984 | European Pat. Off. . |
| 0196841 | 10/1986 | European Pat. Off. . |
| 812859 | 3/1982 | Finland . |
| 813034 | 4/1982 | Finland . |
| 813283 | 4/1982 | Finland . |
| 813422 | 5/1982 | Finland . |
| 2491469 | 4/1982 | France . |
| 3143946 | 10/1982 | Germany . |
| 32 27 055.0 | 3/1983 | Germany . |
| 3226768 | 5/1983 | Germany . |
| 32 46 757.5 | 9/1983 | Germany . |
| 3211397 | 11/1983 | Germany . |
| 3322530 | 10/1985 | Germany . |
| 64085 | 12/1986 | Israel . |
| 57-77672 | 5/1982 | Japan . |
| 57-88164 | 6/1982 | Japan . |
| 57-91974 | 6/1982 | Japan . |
| 57-112359 | 7/1982 | Japan . |
| 162561 | 9/1983 | Japan . |
| 172367 | 10/1983 | Japan . |
| 198535 | 9/1984 | New Zealand . |
| 198702 | 8/1985 | New Zealand . |
| 81/5988 | 8/1982 | South Africa . |
| 82/8085 | 9/1983 | South Africa . |
| 83/2229 | 12/1983 | South Africa . |
| 2086390 | 5/1982 | United Kingdom . |
| 2095682 | 10/1982 | United Kingdom . |

OTHER PUBLICATIONS

Dorland's Medical Dictionary, 24th Ed (1965), W.B Saunders Co. pp. 649 and 746.
Effect of Ramipril on Mortality and Morbidity of Survivors of Acute Myocardial Infaction with Clinical Evidence of Heart Failure, The Acute Infaction Ramipril Efficacy (AIRE) Study Investigators, The Lancet, Oct. 2, 1993, vol. 342, No. 8875.
Drug Evaluations, 6th Ed. (1986), American Medical Assn., pp. 429–434 and 535–536.
Teetz, CA(100):52012h (1984), p. 617.
Urbach, CA(100):139616g (1984), p. 702.
Urbach, CA(100):139617h (1984), p. 702.
Henning, CA(100):210436f (1984), p. 655.
Geiger, CA(97):92759h (1982), p. 819.
Leonard et al., J. Am. Chem. Soc., 77, 439 (1955).
Leonard et al., J. Am. Chem. Soc., 78, 3457 (1956).
Leonard et al., J. Am. Chem. Soc., 78, 3463 (1956).
Leonard et al., J. Am. Chem. Soc., 81, 5627 (1959).
Koelsch et al., J. Org. Chem., 26, 1104 (1961).
Griot et al., Helv. Chim. Acta, 42, 121 (1959).
Bonnett et al., J. Chem. Soc., 2087 (1959).
Battersby et al., J. Chem. Soc., 4333 (1958).
Rosenblatt et al., The Chemistry of Functional Groups, Supplement F: The Chemistry of Amino, Nitroso and Nitro Compounds and Their Derivatives, Part II, S. Patai, ed., Wiley & Sons: New York, 1982, pp. 1100–1104.
L.W. Haynes, Enamines, A.G. Cook, ed., Marcel Decker, Inc.: 1969, pp. 68–79, 261–269, 413.
Fieser & Fieser, Reagents for Organic Synthesis, vol. 1, pp. 644–651 (1967).

Boehme et al., Iminium Salts in Organic Chemistry, Part I (E.C. Taylor, ed.), Wiley & Sons: New York, 1976, p. 143.
S. Dayagi et al., The Chemistry of Functional Groups, The Chemistry of the Carbon–Nitrogen Double Bond, S. Patai, ed., Wiley & Sons: New York, 1970, p. 119.
W. Greenlee et al., J. Med. Chem., 28, 434,442 (1985).
K. Ogawa et al., J. Chem. Soc., Perkin Trans. I, 3031–3035 (1982).
R. Bacon and D. Stewart, J. Chem. Soc. (C), 1384–1387 (1966).
R. Bacon et al., J. Chem. Soc. (C), 1388–1389 (1966).
Patchett et al., Nature, 288, 280–283 (1980).
Booth et al., Chemistry and Industry, 466–467 (1956).
Booth et al., J. Chem. Soc., Part I, 1050–1054 (1959).
Murakoshi et al., Chemical Abstracts, 61, 9465(e) (1964).
Cushman et al., Fed. Proc., 38 (13), 2778–2782 (1979).
Houben–Weyl, Methoden er Organischen Chemie, 7(2b), 1403–1404 (1976).
Katritskaya, Dzh. Lagorskaya Khimia Geterosikl. Soedin., Moskow, 1963, pp. 155–158.
Anderson, Jr. et al., J. Org. Chem., 43(1), 54–57 (1978).
Bertho et al., Synthesen In Der 2–Azabicyclo[0.3.3]–octan--Reihe, Chemische Berichte, 92(7), 2218–2235 (1959).
Farkas et al., J. Org. Chem., 22, 1261–1263 (1957).
Taylor et al., J. Org. Chem., 38(16), 2817–2821 (1973).
Taylor et al., Heterocycles, 25, 343–345 (1987).
English language translation of Mitzlaff et al., Liebig's Ann. Chem., 1713–1733 (1978).
Quarterly Reviews 25: 323–341 (1971).
Chem. Berichte 86: 1524–1528 (1953).
Chem. Abst. 49/1955/3009c.
Xiang et al. Chem. Abstracts, CA (100):150853c (1984), p. 3.
Teetz et al., Chemical Abstract, vol. 99, No. 158854k (1983).
Gross, F., Chemical Abstract, vol. 100, No. 1510369 (1983).
Urbach et al., Chemical Abstract, vol. 103, No. 160858 (1985).
Stedman's Medical Dictionary, 22nd Ed. (1972), The Williams and Wilkins Company, Baltimore, p. 638.
The Merck Manual, 15th Ed. (1987), Berkow M.D. editor, pp. 401, 428–429.
Gavras et al., Circulation, vol. 58, No. 5 (1978), pp. 770–776.
Ader et al., Circulation, vol. 61,. No. 5 (1980), pp. 931–937.
Bernward Schölkens et al., "Experimental Cardiovascular Benefits of Angiotensin—Converting Enzyme Inhibitors: Beyond Blood Pressure Reduction," J. Cardiovasc. Pharmacol., vol. 18 (Supp. 2), pp. S26–S30 (1991).
A. Gavazzi, R. Marioni, C. Campana & C. Montemartini, Comparative trial of quinapril versus captopril in mild to moderate congestive heart failure, Journal of Hypertension, 1994, 12 (suppl 4); 589–593.
D. Canter, G. Frank, L. Knapp and R. McLain, The Safety Profile of Quinapril: Is There a Difference Among ACE Inhibitors?, Clin. Cardiol. 13, VII–39–42 (1990).
Ryozo Koshiura et al., "Naibumpi Yakuri" (Endocrinological Pharmacology) pp. 136–137 (Jun. 10, 1983) (w/English translation of passages).

METHOD OF TREATING CARDIAC INSUFFICIENCY USING ANGIOTENSIN-CONVERTING ENZYME INHIBITORS

This is a continuation of application Ser. No. 08/445,543, filed May 22, 1995, now U.S. Pat. No. 5,684,016, which is a divisional application Ser. No. 08/359,860, filed Dec. 20, 1994, which is a divisional of application Ser. No. 08/188,745, filed Jan. 31, 1994, now U.S. Pat. No. 5,403,856, which is a continuation of application Ser. No. 07/920,173, filed Jul. 27, 1992, abandoned, which is a continuation of application Ser. No. 07/636,001, filed Jan. 3, 1991, abandoned, which is a continuation of application Ser. No. 07/313,491, filed Feb. 22, 1989, abandoned, which is a continuation of application Ser. No. 06/721,705, filed Apr. 10, 1985, abandoned.

The invention relates to a method of treating cardiac insufficiency by peroral or parenteral use of angiotensin-converting enzyme inhibitors of the formula I

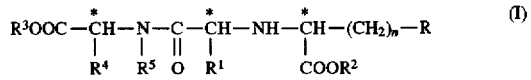

in which n is 1 or 2,

R denotes hydrogen,
- an optionally substituted aliphatic radical with 1–8 carbon atoms,
- an optionally substituted alicyclic radical with 3–9 carbon atoms,
- an optionally substituted aromatic radical with 6–12 carbon atoms,
- an optionally substituted araliphatic radical with 7–14 carbon atoms,
- an optionally substituted alicyclic-aliphatic radical with 7–14 carbon atoms, or
- a radical $OR^a$ or $SR^a$, in which $R^a$ represents an optionally substituted aliphatic radical with 1–4 carbon atoms, an optionally substituted aromatic radical with 6–12 carbon atoms or an optionally substituted heteroaromatic radical with 5–12 ring atoms, $R^1$ denotes hydrogen,
- an optionally substituted aliphatic radical with 1–6 carbon atoms,
- an optionally substituted alicyclic radical with 3–9 carbon atoms,
- an optionally substituted alicyclic-aliphatic radical with 4–13 carbon atoms,
- an optionally substituted aromatic radical with 6–12 carbon atoms,
- an optionally substituted araliphatic radical with 7–16 carbon atoms,
- an optionally substituted heteroaromatic radical with 5–12 ring atoms or
- a naturally occurring α-amino acid, protected in the side chain if necessary, $R^2$ and $R^3$ are identical or different and denote hydrogen,
- an optionally substituted aliphatic radical with 1–6 carbon atoms,
- an optionally substituted alicyclic radical with 3–9 carbon atoms,
- an optionally substituted aromatic radical with 6–12 carbon atoms or
- an optionally substituted araliphatic radical with 7–16 carbon atoms and $R^4$ and $R^5$, together with the atoms carrying them, form a heterocyclic mono-, bi- or tri-cyclic ring system with 5 to 15 carbon atoms.

Possible ring systems are, in particular, those of the following group: tetrahydroisoquinoline (A); decahydroisoquinoline (B); octahydroindole (C); octahydrocyclopenta[b]pyrrole (D); 2-azaspiro[4.5]decane (E); 2-azaspiro[4.4]nonane (F); spiro[(bicyclo[2.2.1]heptane)-2,3-pyrrolidine] (G); spiro[(bicyclo[2.2.2]octane)-2,3-pyrrolidine] (J); 2-azatricyclo[4.3.0.1$^{6,9}$]decane (I); decahydrocyclohepta[b]pyrrole (J); octahydroisoindole (K); octahydrocyclopenta[c]pyrrole (L); 2,3,3a,4,5,7a-hexahydroindole (M); 2-azabicyclo[3.1.0]hexane (N); all of which can optionally be substituted. However, the unsubstituted systems are preferred.

In the case of the compounds which possess several chiral atoms, all the possible diastereomers, as racemates or enantiomers, or mixtures of various diastereomers, are suitable.

The possible cyclic amino acid esters have the following structural formulae:

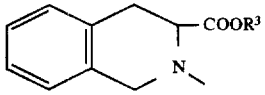
A

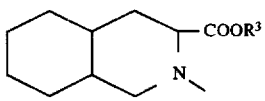
B

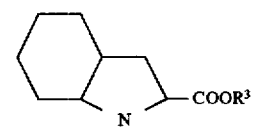
C

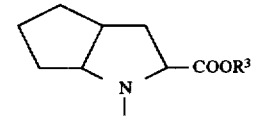
D

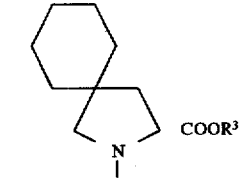
E

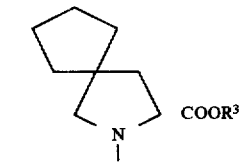
F

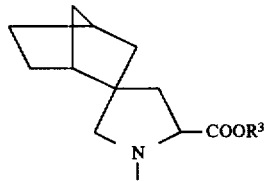
G

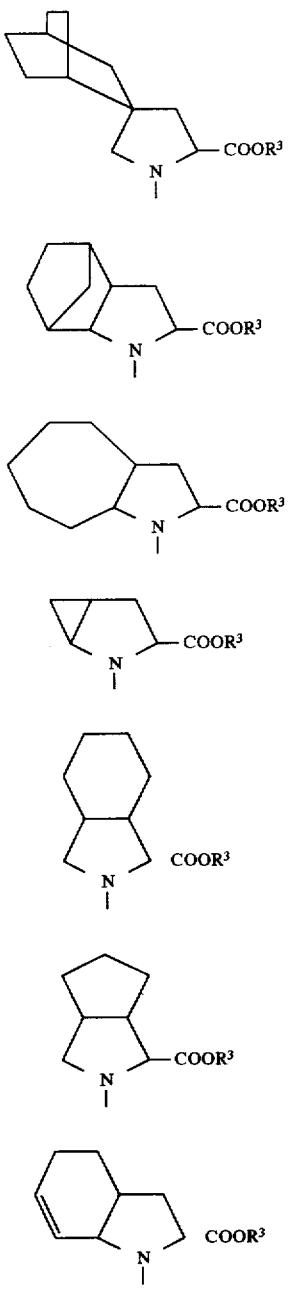

A preferred embodiment comprises the use of compounds of the formula I in which n is 1 or 2, R denotes hydrogen, alkyl with 1–8 carbon atoms, alkenyl with 2–6 carbon atoms, cycloalkyl with 3–9 carbon atoms, aryl with 6–12 carbon atoms, which can be mono-, di- or tri-substituted by ($C_1$–$C_4$)-alkyl, ($C_1$–$C_4$)-alkoxy, hydroxyl, halogen, nitro, amino, aminomethyl, ($C_1$–$C_4$)-alkylamino, di-($C_1$–$C_4$)-alkylamino, ($C_1$–$C_4$)-alkanoylamino, methylenedioxy, carboxyl, cyano and/or sulfamyl, alkoxy with 1–4 carbon atoms, aryloxy with 6–12 carbon atoms, which can be substituted as described above for aryl, mono- or bi-cyclic heteroaryloxy with 5–7 or 8–10 ring atoms, in which 1 or 2 ring atoms are sulfur or oxygen atoms and/or 1 to 4 ring atoms are nitrogen, which can be substituted as described above for aryl, amino-($C_1$–$C_4$)-alkyl, ($C_1$–$C_4$)-alkanoylamino-($C_1$–$C_4$)-alkyl, ($C_7$–$C_{13}$)-aroylamino-($C_1$–$C_4$)-alkyl, ($C_1$–$C_4$)-alkoxycarbonylamino-($C_1$–$C_4$)-alkyl, ($C_6$–$C_{12}$)-aryl-($C_1$–$C_4$)-alkoxycarbonylamino-($C_1$–$C_4$)-alkyl, ($C_6$–$C_{12}$)-aryl-($C_1$–$C_4$)-alkylamino-($C_1$–$C_4$)-alkyl, ($C_1$–$C_4$)-alkylamino-($C_1$–$C_4$)-alkyl, di-($C_1$–$C_4$)-alkylamino-($C_1$–$C_4$)-alkyl, guanidino-($C_1$–$C_4$)-alkyl, imidazolyl, indolyl, ($C_1$–$C_4$)-alkylthio, ($C_1$–$C_4$)-alkylthio-($C_1$–$C_4$)-alkyl, ($C_6$–$C_{12}$)-arylthio-($C_1$–$C_4$)-alkyl, which can be substituted in the aryl part as described above for aryl, ($C_6$–$C_{12}$)-aryl-($C_1$–$C_4$)-alkylthio, which can be substituted in the aryl part as described above for aryl, carboxy-($C_1$–$C_4$)-alkyl, carboxyl, carbamyl, carbamyl-($C_1$–$C_4$)-alkyl, ($C_1$–$C_4$)-alkoxy-carbonyl-($C_1$–$C_4$)-alkyl, ($C_6$–$C_{12}$)-aryloxy-($C_1$–$C_4$)-alkyl, which can be substituted in the aryl part as described above for aryl, or ($C_6$–$C_{12}$)-aryl-($C_1$–$C_4$)-alkoxy, which can be substituted in the aryl part as described above for aryl, $R^1$ denotes hydrogen, alkyl with 1–6 carbon atoms, alkenyl with 2–6 carbon atoms, alkynyl with 2–6 carbon atoms, cycloalkyl with 3–9 carbon atoms, cycloalkenyl with 5–9 carbon atoms, ($C_3$–$C_9$)-cycloalkyl-($C_1$–$C_4$)-alkyl, ($C_5$–$C_9$)-cycloalkenyl-($C_1$–$C_4$)-alkyl, optionally partly hydrogenated aryl with 6–12 carbon atoms, which can be substituted as described above for R, ($C_6$–$C_{12}$)-aryl-($C_1$–$C_4$)-alkyl or ($C_7$–$C_{13}$)-aroyl-($C_1$ or $C_2$)-alkyl both of which can be substituted as the above aryl, mono- or bi-cyclic, optionally partly hydrogenated heteroaryl with 5–7 or 8–10 ring atoms, in which 1 or 2 ring atoms are sulfur or oxygen atoms and/or 1 to 4 ring atoms are nitrogen atoms, which can be substituted as the above aryl, or the side chain, protected if necessary, of a naturally occurring -amino acid $R^1$—CH($NH_2$)—COOH, $R^2$ and $R^3$ are identical or different and denote hydrogen, alkyl with 1–6 carbon atoms, alkenyl with 2–6 carbon atoms, di-($C_1$–$C_4$)-alkylamino-($C_1$–$C_4$)-alkyl, ($C_1$–$C_5$)-alkanoyloxy-($C_1$–$C_4$)-alkyl, ($C_1$–$C_6$)-alkoxy-carbonyloxy-($C_1$–$C_4$)-alkyl, ($C_7$–$C_{13}$)-aroyloxy-($C_1$–$C_4$)-alkyl, ($C_6$–$C_{12}$)-aryloxycarbonyloxy($C_1$–$C_4$)-alkyl, aryl with 6–12 carbon atoms, ($C_6$–$C_{12}$)-aryl-($C_1$–$C_4$)-alkyl, ($C_3$–$C_9$)-cycloalkyl or ($C_3$–$C_9$)-cycloalkyl-($C_1$–$C_4$)-alkyl and $R^4$ and $R^5$ have the abovementioned meaning.

A particularly preferred embodiment comprises use of compounds of the formula I in which n is 1 or 2, R denotes ($C_1$–$C_6$)-alkyl, ($C_2$–$C_6$)-alkenyl, ($C_3$–$C_9$)-cycloalkyl, amino-($C_1$–$C_4$)-alkyl, ($C_2$–$C_5$)-acylamino-($C_1$–$C_4$)-alkyl, ($C_7$–$C_{13}$)-aroylamino-($C_1$–$C_4$)-alkyl, ($C_1$–$C_4$)-alkoxy-carbonylamino-($C_1$–$C_4$)-alkyl, ($C_6$–$C_{12}$)-aryl-($C_1$–$C_4$)-alkoxycarbonylamino-($C_1$–$C_4$)-alkyl, ($C_6$–$C_{12}$)-aryl, which can be mono-, di- or tri-substituted by ($C_1$–$C_4$)-alkyl, ($C_1$–$C_4$)-alkoxy, hydroxyl, halogen, nitro, amino, ($C_1$–$C_4$)-alkylamino, di-($C_1$–$C_4$)-alkylamino and/or methylenedioxy, or denotes 3-indolyl, in particular methyl, ethyl, cyclohexyl, tert.-butoxycarbonylamino-($C_1$–$C_4$)-alkyl, benzoyloxycarbonylamino-($C_1$–$C_4$)-alkyl or phenyl, which can be mono- or di-substituted by phenyl, ($C_1$–$C_2$)-alkyl, ($C_1$ or $C_2$)-alkoxy, hydroxyl, fluorine, chlorine, bromine, amino, ($C_1$–$C_4$)-alkylamino, di-($C_1$–$C_4$)alkylamino, nitro and/or methylenedioxy, or, in the case of methoxy, can be trisubstituted, $R^1$ denotes hydrogen or ($C_1$–$C_6$)-alkyl, which can optionally be substituted by amino, ($C_1$–$C_6$)-acylamino or benzoylamino, ($C_2$–$C_6$)-alkenyl, ($C_3$–$C_9$)-cycloalkyl, ($C_5$–$C_9$)-cycloalkenyl, ($C_3$–$C_7$)-cycloalkyl-($C_1$–$C_4$)-alkyl, ($C_6$–$C_{12}$)-aryl or partly hydrogenated aryl, which can in each case be substituted by ($C_1$–$C_4$)-alkyl, ($C_1$ or $C_2$)-alkoxy or halogen, ($C_6$–$C_{12}$)-aryl-($C_1$ to $C_4$)-alkyl or ($C_7$–$C_{13}$)-aroyl-($C_1$–$C_2$)-alkyl, both of which can be substituted in the aryl radical as defined above, a mono- or bi-cyclic heterocyclic radical with 5 to 7 or 8 to 10 ring atoms, in which 1 or 2 ring atoms are sulfur or oxygen atoms and/or 1 to 4 ring atoms are nitrogen atoms, or a side chain of a naturally occurring α-amino acid, which is protected if necessary, but in particular hydrogen, ($C_1$–$C_3$)-alkyl, ($C_2$ or $C_3$)-alkenyl, the side chain, protected if necessary, of lysine, benzyl, 4-methoxybenzyl, 4-ethoxybenzyl, phenethyl, 4-amino-butyl or benzoylmethyl, $R^2$ and $R^3$ denote identical or different radicals from the group comprising hydrogen, ($C_1$–$C_6$)-alkyl, ($C_2$–$C_6$)-alkenyl and ($C_6$–$C_{12}$)-aryl-($C_1$–$C_4$)-alkyl, but in particular hydrogen, ($C_1$–$C_4$)-alkyl or benzyl and $R^4$ and $R^5$ have the abovementioned meaning.

It is particularly preferred to use compounds of the formula I in which n is 2, R=phenyl, $R^1$=methyl, $R^2$ and $R^3$ denote identical or different ($C_1$–$C_6$)-alkyl radicals or ($C_7$–$C_{10}$)-aralkyl radicals, such as benzyl or nitrobenzyl, and $R^4$ and $R^5$ together represent a radical of the formula

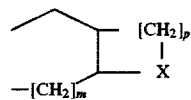

in which m denotes 0 or 1, p denotes 0, 1 or 2 and X denotes —$CH_2$—, —$CH_2$—$CH_2$— or —CH=CH—, it also being possible for a 6-membered ring formed with X to be a benzene ring.

Aryl here and in the following text is preferably to be understood as optionally substituted phenyl, bi-phenylyl or naphthyl. Corresponding statements apply to radicals derived from aryl, such as aryloxy and arylthio. Aroyl is understood as being, in particular, benzoyl. Aliphatic radicals can be straight-chain or branched.

A monocyclic or bicyclic heterocyclic radical with 5 to 7 or 8 to 10 ring atoms, 1 or 2 ring atoms of which are sulfur or oxygen atoms and/or 1 to 4 ring atoms of which are nitrogen atoms, is understood as meaning, for example, thienyl, benzo[b]thienyl, furyl, pyranyl, benzofuryl, pyrrolyl, imidazolyl, pyrazolyl, pyridyl, pyrimidinyl, pyridazinyl, indazolyl, isoindolyl, indolyl, purinyl, quinolizinyl, isoquinolinyl, phthalazinyl, naphthyridinyl, quinoxalinyl, quinazolyl, cinnolinyl, pteridinyl, oxyzolyl, isoxazolyl, thiazolyl or isothiazolyl. These radicals can also be partly or completely hydrogenated.

Naturally occurring α-amino acids are described, for example, in Houben-Weyl, Methoden der Organischen Chemie (Methods of Organic Chemistry), Volume XV/1 and XV/2.

If $R^1$ represents a side chain of a protected naturally occurring α-amino acid, such as, for example, protected Ser, Thr, Asp, Asn, Glu, Gln, Arg, Lys, Hyl, Cys, Orn, Cit, Tyr, Trp, His or Hyp, groups which are customary in peptide chemistry are preferred as the protective groups (c.f. Houben-Weyl, Volume XV/1 and XV/2). In the case where $R^1$ denotes the protected lysine side chain, the known amino-protective groups are preferred, but especially Z, Boc or ($C_1$–$C_6$)-alkanoyl. Possible O-protective groups for tyrosine are, preferably, ($C_1$–$C_6$)-alkyl, in particular methyl or ethyl.

The following compounds can be particularly advantageously used by the method according to the invention:

N-(1-S-carbethoxy-3-phenyl-propyl)-S-alanyl-S-1,2,3,4-tetrahydroisoquinoline-3-carboxylic acid N-(1-S-carbethoxy-3-cyclohexyl-propyl)-S-alanyl-S-1,2,3,4-tetrahydroisoquinoline-3-carboxylic acid N-(1-S-carbethoxy-3-phenyl-propyl)-S-lysyl-S-1,2,3,4-tetrahydroisoquinoline-3-carboxylic acid N-(1-S-carbethoxy-3-phenyl-propyl)-O-ethyl-S-tyrosyl-S-1,2,3,4-tetrahydroisoquinoline-3-carboxylic acid N-(1-S-carbethoxy-3-phenyl-propyl)-S-alanyl-3S-decahydroisoquinoline-3-carboxylic acid N-(1-S-carbethoxy-3-phenyl-propyl)-S-alanyl-(2S,3aS,7aS)-octahydroindole-2-carboxylic acid N-(1-S-carbethoxy-3-cyclohexyl-propyl)-S-alanyl-(2S,3aS,7aS)-octahydroindole-2-carboxylic acid N-(1-S-carbethoxy-3-phenyl-propyl)-S-lysyl-(2S,3aS,7aS)-octahydroindole-2-carboxylic acid N-(1-S-carbethoxy-3-cyclohexyl-propyl)-S-lysyl-(2S,3aS,7aS)-octahydroindole-2-carboxylic acid N-(1-S-carbethoxy-3-cyclohexyl-propyl)-S-lysyl-(2S,3aS,7aS)-octahydroindole-2-carboxylic acid N-(1-S-carbethoxy-3-phenyl-propyl)-O-methyl-S-tyrosyl-(2S,3aS,7aS)-octahydroindole-2-carboxylic acid N-(1-S-carbethoxy-3-phenyl-propyl)-O-ethyl-S-tyrosyl-(2S,3aS,7aS)-octahydroindole-2-carboxylic acid N-(1-S-carbethoxy-3-(3,4-dimethylphenyl-propyl)-S-alanyl-(2S,3aS,7aS)-octahydroindole-2-carboxylic acid N-[1-S-carbethoxy-3-(4-fluorophenyl)-propyl]-S-alanyl-(2S,3aS,7aS)-octahydroindole-2-carboxylic acid N-[1-S-carbethoxy-3-(4-methoxyphenyl)-propyl]-S-alanyl-(2S,3aS,7aS)-octahydroindole-2-carboxylic acid N-[1-S-carbethoxy-3-(3,4-dimethoxyphenyl)-propyl]-S-alanyl-(2S,3aS,7aS)-octahydroindole-2-carboxylic acid N-(1-S-carbethoxy-3-cyclopentylpropyl)-S-alanyl-(2S,3aS,7aS)-octahydroindole-2-carboxylic acid N-(1-S-carbethoxy-3-phenyl-propyl)-S-alanyl-(2S,3aR,7aS)-octahydroindole-2-carboxylic acid N-(1-S-carbethoxy-3-cyclohexyl-propyl)-S-alanyl-(2S,3aR,7aS)-octahydroindole-carboxylic acid N-(1-S-carbethoxy-3-phenyl-propyl)-S-lysyl-(2S,3aR,7aS)-octahydroindole-2-carboxylic acid N-(1-S-carbethoxy-3-cyclohexyl-propyl)-S-lysyl-(2S,3aR,7aS)-octahydroindole-2-carboxylic acid N-(1-S-carbethoxy-3-phenyl-propyl)-O-ethyl-S-tyrosyl-(2S,3aS,7aR)-octahydroindole-2-carboxylic acid N-(1-S-carbethoxy-3-phenyl-propyl)-S-alanyl-(2S,3aR,7aR)-octahydroindole-2-carboxylic acid N-(1-S-carbethoxy-3-phenyl-propyl)-S-lysyl-(2S,3aR,7aS)-octahydroindole-2-carboxylic acid N-(1-S-carbethoxy-3-cyclohexyl-propyl)-S-alanyl-(2S,3aR,7aR)-octahydroindole-2-carboxylic acid N-(1-S-carbethoxy-3-cyclohexyl-propyl)-O-ethyl-S-tyrosyl-(2S,3aR,7aR)-octahydroindole-2-carboxylic acid N-(1-S-carbethoxy-3-phenyl-propyl)-S-alanyl-(2S,3aS,7aR)-octahydroindole-2-carboxylic acid N-(1-S-carbethoxy-3-phenyl-propyl)-O-ethyl-S-tyrosyl-(2S,3aS,7aS)-octahydroindole-2-carboxylic acid N-(1-S-carbethoxy-3,4-dimethylphenyl-propyl)-S-alanyl-(2S,3aS,7aS)-octahydroindole-2-carboxylic acid N-[1-S-carbethoxy-3-(4-fluorophenyl)-propyl]-S-alanyl-(2S,3aS,7aS)-octahydroindole-2-carboxylic acid N-[1-S-carbethoxy-3-(4-methoxyphenyl)-propyl]-S-alanyl-(2S,3aS,7aS)-octahydroindole-2-carboxylic acid N-[1-S-carbethoxy-3-(3,4-dimethoxyphenyl)-propyl]-S-alanyl-(2S,3aS,7aS)-octahydroindole-2-carboxylic acid N-(1-S-carbethoxy-3-cyclopentylpropyl)-S-alanyl-(2S,3aS,7aS)-octahydroindole-2-carboxylic acid N-(1-S-carbethoxy-3-phenyl-propyl)-S-alanyl-cis-endo-2-azabicyclo[3.3.0]octane-3-S-carboxylic acid N-(1-S-carbethoxy-3-phenyl-propyl)-S-lysyl-cis-endo-2-azabicyclo[3.3.0]octane-3-S-carboxylic acid N-(1-S-carbethoxy-3-cyclohexyl-propyl)-S-alanyl-cis-endo-2-azabicyclo[3.3.0]octane-3-S-carboxylic acid N-(1-S-carboxy-3-cyclohexyl-propyl)-S-alanyl-cis-endo-2-azabicyclo[3.3.0]octane-3-S-carboxylic acid N-(1-S-carbethoxy-butyl)-S-alanyl-cis-endo-2-azabicyclo[3.3.0]octane-3-S-carboxylic acid N-(1-S-carbethoxy-3-(3,4-dimethoxyphenylpropyl)-S-alanyl-cis-endo-2-azabicyclo[3.3.0]octane-3-S-carboxylic acid N-(1-S-carbethoxy-3-cyclopentyl-propyl)-S-alanyl-cis-endo-azabicyclo[3.3.0]octane-3-S-carboxylic acid N-(1-S-carbethoxy-3-phenyl-propyl)-O-methyl-S-tyrosyl-cis-endo-2-azabicyclo[3.3.0]octane-3-S-carboxylic acid N-(1-S-carbethoxy-3-phenyl-propyl)-O-ethyl-S-tyrosyl-cis-endo-2-azabicyclo[3.3.0]octane-3-S-carboxylic acid N-(1-S-carbethoxy-3-(4-fluorophenyl-propyl)-S-alanyl-cis-endo-azabicyclo[3.3.0]octane-3-S-carboxylic acid N-(1-S-carbethoxy-3-(4-methoxyphenyl-propyl)-S-alanyl-cis-endo-2-azabicyclo[3.3.0]octane-3-S-carboxylic acid N-(1-S-carbethoxy-3-phenyl-propyl)-S-lysyl-(2S,3aR,6aS)-octahydrocyclopenta[b]pyrrole-2-carboxylic acid N-(1-S-carbethoxy-3-cyclohexylpropyl)-lysyl-(2S,3a,6aS)-octahydrocyclopenta[b]pyrrole-2-carboxylic acid N-(1-S-carbethoxy-3-phenyl-propyl)-O-ethyl-S-tyrosyl-(2S,3aR,6aS)-octahydrocyclopenta[b]pyrrole-2-carboxylic acid N-(1-S-carbethoxy-3-phenyl-propyl)-S-alanyl-2-(2S,3aR,6aS)-octahydrocyclopenta[b]pyrrole-2-carboxylic acid N-(1-S-carbethoxy-3-phenyl-propyl)-S-alanyl-2-azaspiro[4,5]decane-3-S-carboxylic acid N-(1-S-carbethoxy-3-phenyl-propyl)-O-ethyl-2-tyrosyl-azaspiro-[4,5]decane-3-S-carboxylic acid N-(1-S-carbethoxy-3-phenyl-propyl)-S-lysyl-2-azaspiro[4,5]decane-3-S-carboxylic acid N-(1-S-carbethoxy-3-cyclohexylpropyl)-S-alanyl-2-azaspiro[4,5]decane-3-S-carboxylic acid N-(1-S-carbethoxy-3-cyclohexylpropyl)-S-lysyl-2-azaspiro[4,5]decane-3-S-carboxylic acid N-(1-S-carbethoxy-3-phenyl-propyl)-S-alanyl-2-azaspiro[4,4]nonane-3-S-carboxylic acid N-(1-S-carbethoxy-3-phenyl-propyl)-O-ethyl-S-tyrosyl-2-azaspiro[4,4]nonane-3-S-carboxylic acid N-(1-S-carbethoxy-3-phenyl-propyl)-S-lysyl-2-azaspiro[4,4]nonane-3-S-carboxylic acid N-(1-S-carbethoxy-3-cyclohexyl-propyl)-S-alanyl-2-azaspiro[4,4]nonane-3-S-carboxylic acid N-(1-S-carbethoxy-3-cyclopentyl-propyl)-S-alanyl-2-azaspiro[4,4]nonane-3-S-carboxylic acid N-(1-S-carbethoxy-3-cyclopentyl-propyl)-S-lysyl-2-azaspiro[4,4]nonane-3-S-carboxylic acid N-(1-S-carbethoxy-3-phenyl-propyl)-S-alanyl-spiro[bicyclo[2.2.1]heptane-2,3'-pyrrolidine]-5'-S-carboxylic acid.

N-(1-S-carbethoxy-3-phenyl-propyl)-O-ethyl-S-tyrosyl-spiro[bicyclo[2.2.1]heptane-2,3'-pyrrolidine]-5'-S-carboxylic acid N-(1-S-carbethoxy-3-phenyl-propyl)-S-lysyl-spiro[bicyclo[2.2.1]heptane-2,3'-pyrrolidine]-5'-S-carboxylic acid N-(1-S-carbethoxy-3-cyclohexyl-propyl)-S-alanyl-spiro[bicyclo[2.2.1]heptane-2,3'-pyrrolidine]-5'-S-carboxylic acid N-(1-S-carbethoxy-3-cyclohexyl-propyl)-S-lysyl-spiro[bicyclo[2.2.1]heptane-2,3'-pyrrolidine]-5'-S-carboxylic acid N-(1-S-carbethoxy-3-phenyl-propyl)-S-alanyl-spiro[bicyclo[2.2.2]octane-2,3'-pyrrolidine]-5'-S-carboxylic acid N-(1-S-carbethoxy-3-phenyl-propyl)-O-ethyl-tyrosyl-spiro[bicyclo[2.2.2]octane-2,3'-pyrrolidine]-5'-S-carboxylic acid N-(1-S-carbethoxy-3-phenyl-propyl)-S-lysyl-spiro[bicyclo[2.2.2]octane-2,3'-pyrrolidine]-5'-S-carboxylic acid N-(1-S-carbethoxy-3-cyclohexyl-propyl)-S-alanyl-spiro[bicyclo[2.2.2]octane-2,3'-pyrrolidine]-5'-S-carboxylic acid N-(1-S-carbethoxy-3-phenyl-propyl)-S-alanyl-2-azatricyclo[4.3.0.1$^{6,9}$]decane-3-S-carboxylic acid N-(1-S-carbethoxy-3-phenyl-propyl)-O-ethyl-S-tyrosyl-2-azatricyclo[4.3.0.1$^{6,9}$]decane-3-S-carboxylic acid N-(1-S-carbethoxy-3-phenyl-propyl)-S-lysyl-2-azatricyclo[4.3.0.1$^{6,9}$]decane-3-S-carboxylic acid N-(1-S-carbethoxy-3-cyclohexyl-propyl)-S-alanyl-2-azatricyclo[4.3.0.1$^{6,9}$]decane-3-S-carboxylic acid N-(1-S-carbethoxy-3-cyclohexyl-propyl)-S-lysyl-2-azatricyclo[4.3.0.1$^{6,9}$]decane-3-S-carboxylic acid N-(1-S-carbethoxy-3-phenyl-propyl)-S-alanyl-decahydrocyclohepta[b]pyrrole-2-S-carboxylic acid N-(1-S-carbethoxy-3-phenyl-propyl)-O-ethyl-S-tyrosyldecahydrocyclohepta[b]pyrrole-2-S-carboxylic acid N-(1-S-carbethoxy-3-phenyl-propyl)-S-lysyl-decahydrocyclohepta[b]pyrrole-2-S-carboxylic acid N-(1-S-carbethoxy-3-cyclohexyl-propyl)-S-alanyl-decahydrocyclohepta[b]pyrrole-2-S-carboxylic acid N-(1-S-carbethoxy-3-cyclohexyl-propyl)-S-lysyl-decahydrocyclohepta[b]pyrrole-2-S-carboxylic acid N-(1-S-carbethoxy-3-phenyl-propyl)-S-alanyl-trans-octahydroisoindole-1-S-carboxylic acid N-(1-S-carbethoxy-3-phenyl-propyl)-S-alanyl-cis-octahydroisoindole-1-S-carboxylic acid N-(1-S-carbethoxy-3-cyclohexyl-propyl)-S-alanyl-transoctahydroisoindole-1-S-carboxylic acid N-(1-S-carbethoxy-3-cyclohexyl-propyl)-S-alanyl-cis-octahydroisoindole-1-S-carboxylic acid N-(1-S-carbethoxy-3-phenyl-propyl)-S-alanyl-cis-octahydrocyclopenta[b]pyrrole-1-S-carboxylic acid benzyl N-(1-S-carbethoxy-3-cyclohexyl-propyl)-S-alanyl-cis-octahydrocyclopenta[c]pyrrole-1-carboxylate N-(1-S-carbethoxy-3-cyclohexyl-propyl)-S-lysyl-cis-octahydrocyclopenta[c]pyrrole-1-S-carboxylic acid N-(1-S-carbethoxy-3-phenyl-propyl)-S-alanyl-2,3,3a,4,5,7a-hexahydroindole-cis-endo-2-S-carboxylic acid N-(1-S-carbethoxy-3-phenyl-propyl)-S-lysyl-2,3,3a,4,5,7a-hexahydroindole-cis-endo-2-S-carboxylic acid N-(1-S-carbethoxy-3-cyclohexyl-propyl)-S-lysyl-2-azabicyclo[3.1.0]hexane-3-S-carboxylic acid N-(1-S-carbethoxy-3-phenyl-propyl)-S-lysyl-2-azabicyclo[3.1.0]hexane-cis-endo-3-S-carboxylic acid N-(1-S-carbethoxy-3-cyclopentylpropyl)-S-alanyl-2-azabicyclo[3.1.0]hexane-3-carboxylic acid N-(1-S-carbethoxy-3-phenyl-propyl)-S-alanyl-cis-endo-2-azabicyclo[3.1.0]hexane-3-S-carboxylic acid and N-(1-S-carbethoxy-3-cyclohexyl-propyl)-S-alanyl-cis-endo-2-azabicyclo[3.1.0]hexane-3-S-carboxylic acid.

These compounds can be prepared, for example, by the process described in German Patent Application P 33 33 455.2, by converting the tert.-butyl or benzyl radicals described in the Application into the monocarboxylic acid derivatives in a known manner by acid or alkaline hydrolysis or by hydrogenolysis catalyzed by a noble metal. The N ε-benzyloxycarbonyl protective group of the lysine derivatives is removed by hydrogenolysis catalyzed by a noble metal. The abovementioned compounds can easily be converted into the corresponding salts (for example hydrochlorides, maleates, fumarates and the like) with physiologically acceptable acids or bases (in the case of mono- or di-carboxylic acids), and can be used according to the invention in the form of the salts.

The compounds of the formula I are inhibitors of angiotensin-converting enzyme (ACE) or intermediates in the preparation of such inhibitors and can also be employed for combating hypertension of various origins. The compounds of the formula I are known from German Offenlegungsschrift 3,211,397, German Offenlegungsschrift 3,227,055, European Patent Application 46,953, European Patent Application 79,022, European Patent Application 84,164, European Patent Application 89,637 and European Patent Application 90,362. They are furthermore the subject of German Patent Applications P 32 42 151.6, P 32 46 503.3, P 32 46 757.5, P 33 00 774.8 and P 33 24 263.1.

In carrying out the method according to the invention, the angiotensin-converting enzyme inhibitors described above can be used on mammals, such as monkeys, dogs, cats, rats, humans and the like. The compounds suitable for the use according to the invention are advantageously incorporated into pharmaceutical products in the usual manner. They can be converted into the customary administration forms, such as capsules, tablets, coated tablets, solutions, ointments and emulsions and also into depot form. If appropriate, the active compound can also be in microencapsulated form. The products can contain acceptable organic or inorganic concomitant substances, for example granulating substances, adhesives and binders, lubricants, suspending agents, solvents, antibacterial agents, wetting agents and preservatives. Oral and parenteral use forms are preferred. The compounds of the formula I can be administered in dosages of 0.1–50 mg per dose once to three times daily.

The efficacy of the compounds of the formula I in various forms of cardiac insufficiency can be derived from their action in various test models. The results with N-(1-S-carbethoxy-3-phenyl-propyl)-S-alanyl-cis-endo-2-azabicyclo[3.3.0]octane-3-S-carboxylic acid (formula II) may in each case serve as examples below.

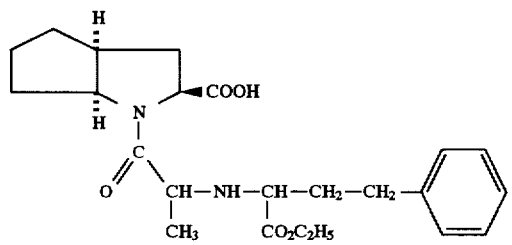

It is known that converting enzyme inhibitors are capable of inhibiting the enzyme not only in the serum but also in various tissues, and especially also in the heart. This inhibition in cardiac tissue reduces the formation of angiotensin II and hence its adverse influences on various parameters of heart action.

Oral treatment of spontaneously hypertensive rats with a single dose of 1 mg/kg significantly inhibits the ACE in the heart for longer than 24 hours. In contrast, with 30 mg/kg of N-(1-carbethoxy-3-phenyl-propyl)-S-alanyl-S-proline (enalapril) perorally, already no further significant inhibition is observed after more than 6 hours. Chronic oral treatment of spontaneously hypertensive rats for two weeks with 1 mg/kg of the compound of the formula II leads to a 55% inhibition of the ACE in the heart at the end of treatment, whilst with 30 mg/kg of enalapril perorally no inhibition is observed, under otherwise identical conditions. In addition, the systemic lowering of blood pressure caused by compounds of the formula I leads to a reduction in the after-load and hence to relief of the incompetent heart.

Postganglionic sympathetic stimulation on the isolated heart leads, via increased catecholamine release, to an increase in heart rate and contractility and to a decrease in coronary blood flow. Oral pretreatment with 1 mg/kg perorally of the compound of the formula I in rabbits significantly reduces the influence on heart rate and coronary blood flow, but leaves the contractility unaffected. These effects act together to protect the incompetent heart.

Angiotensin I decreases whilst bradykinin increases the coronary blood flow in the isolated heart of rabbits, guineapigs and rats. Oral pretreatment of the animals with 1 mg/kg of the compound of the formula I perorally significantly reduces the effect of angiotensin I and increases the action of bradykinin. The same effect can only be achieved with 30 mg/kg of enalapril.

The following examples show the use forms for the treatment of cardiac insufficiency by the method according to the invention. The compounds of the formula I can be converted into the corresponding use forms analogously to the examples.

EXAMPLE 1

Preparation of the agent used according to the invention for oral administration in the treatment of cardiac insufficiency.

1,000 tablets each containing 10 mg of 1-N-(1-S-carbethoxy-3-phenyl-propyl)-S-alanyl-1S,3S,5S-2-azabicyclo[3.3.0]octane-3-carboxylic acid are prepared with the following auxiliaries:

| | |
|---|---|
| N-(1-S-carbethoxy-3-phenyl-propyl)-S-alanyl-1S,3S,5S-2-azabicyclo[3.3.0]octane-3-carboxylic acid | 10 g |
| corn starch | 140 g |
| gelatin | 7.5 g |
| microcrystalline cellulose | 2.5 g |
| magnesium stearate | 2.5 g |

The N-(1-S-carbethoxy-3-phenyl-propyl)-S-alanyl-1S,3S,5S-2-azabicyclo[3.3.0]octane-3-carboxylic acid and corn starch are mixed with an aqueous gelatin solution. The mixture is dried and ground to granules. Microcrystalline cellulose and magnesium stearate are mixed with the granules. The granules formed are compressed to form 1,000 tablets, each tablet containing 10 mg of the ACE inhibitor.

These tablets can be used for the treatment of cardiac insufficiency.

EXAMPLE 2

1,000 tablets each containing 10 mg of N-(1-S-carbethoxy-3-phenyl-propyl)-S-alanyl-(2S,3aR,7aS)-octahydroindole-2-carboxylic acid hydrochloride are produced analogously to Example 1.

EXAMPLE 3

Gelatin capsules each containing 10 mg of N-(1-S-carbethoxy-3-phenyl-propyl)-S-alanyl-1S,3S,5S-2-azabicyclo[3.3.0]octane-3-carboxylic acid are filled with the following mixture:

| | |
|---|---|
| N-(1-S-carbethoxy-3-phenyl-propyl)-S-alanyl-1S,3S,5S-2-azabicyclo[3.3.0]octane-3-carboxylic acid | 10 mg |
| magnesium stearate | 1 mg |
| lactose | 214 mg |

These capsules can be used for the treatment of cardiac insufficiency.

EXAMPLE 4

The preparation of an injection solution for the treatment of cardiac insufficiency is described below:

| | |
|---|---|
| N-(1-S-carbethoxy-3-phenyl-propyl)-S-alanyl-1S,3S,5S-2-azabicyclo[3.3.0]octane-3-carboxylic acid | 250 mg |
| methylparaben | 5 g |
| propylparaben | 1 g |
| sodium chloride | 25 g |
| water for injection purposes | 5 l |

The N-(1-S-carboxy-3-phenyl-propyl)-S-alanyl-1S,3S,5S-2-azabicyclo[3.3.0]octane-3-carboxylic acid, preservatives and sodium chloride are dissolved in 3 L of water for injection purposes and the solution is made up to 5 l with water for injection purposes. The solution is sterile-filtered and filled aseptically into pre-sterilized bottles, which are closed with sterilized rubber caps. Each bottle contains 5 ml of solution.

EXAMPLE 5

Tablets which can be used for the treatment of cardiac insufficiency are prepared as in Example 1, with the difference that instead of N-(1-S-carbethoxy-3-phenyl-propyl)-S-alanyl-1S,3S,5S-2-azabicyclo[3.3.0]-octane-3S-carboxylic acid, N-(1-S-carboxy-3-phenyl-propyl)-S-alanyl-1S,3S,5S-2-azabicyclo[3.3.0]octane-3-carboxylic acid or N-(1-S-carboxy-3-phenyl-propyl)-S-alanyl-2S,3aR,7aS-octahydroindole-2-carboxylic acid or N-(1-S-carbethoxy-3-phenyl-propyl)-S-alanyl-cis-2,3,3a,-4,5,7a-hexahydror[1H]indole-2-S-endo-carboxylic acid or N-(1-S-carboxy-3-phenyl-propyl)-S-alanyl-cis-2,3,4a,4,5,7a-hexahydro[1H]indole-2S-endo-carboxylic acid or N-(1-S-carboxy-3-phenyl-propyl)-S-lysyl-1S,3S,5S-2-azabicyclo-[3.3.0]octane-3-carboxylic acid or N-(1-S-carbethoxy-3-cyclohexyl-propyl)-S-alanyl-1S,3S,5S-2-azabicyclo[3.3.0]-octane-3-carboxylic acid or N-(1-S-carboxy-3-cyclohexyl-propyl)-S-lysyl-1S-3S,5S-2-azabicyclo[3.3.0]octane-3-carboxylic acid is used.

EXAMPLE 6

An injection solution is prepared analogously to the instructions given in Example 4, with the difference that instead of N-(1-S-carbethoxy-3-phenyl-propyl)-S-alanyl-1S,3S,5S-2-azabicyclo[3.3.0]octane-3-carboxylic acid, N-(1-S-carboxy-3-phenyl-propyl)-S-alanyl-1S,3S,5S-2-azabicyclo[3.3.0]octane-3-carboxylic acid or N-(1-S-carbethoxy-3-phenyl-propyl)-S-alanyl-2S,3aR,7aS-octa-hydroindole-2-carboxylic acid hydrochloride or N-(1-S-carboxy-3-phenyl-propyl)-S-alanyl-2S,3aR,7aS-octahydro-indole-2-carboxylic acid or N-(1-S-carbethoxy-3-cyclo-hexyl-propyl)-S-alanyl-cis-2,3,3a,4,5,7a-hexahydro[1H]-indole-2-S-endo-carboxylic acid or N-(1-S-carboxy-3-phenyl-propyl)-S-alanyl-cis-2,3,3a,4,5,7a-hexahydro[1H]-indole-2-S-endo-carboxylic acid or N-(1-carboxy-3-phenyl-propyl)-S-lysyl-1S,3S,5-2-azabicyclo[3.3.0]octane-3-carboxylic acid or N-(1-S-carbethoxy-3-cyclohexyl)-S-alanyl-1S,3S,5S-2-azabicyclo[3.3.0]octane-3-carboxylic acid or N-(1-S-carboxy-3-cyclohexyl-propyl)-S-lysyl-1S,3S,5S-2-azabicyclo[3.3.0]octane-3-carboxylic acid is used.

We claim:

1. A method for treating cardiac insufficiency in a mammal comprising the step of administering to a mammal in recognized need of, and for the purpose of said treatment, an amount of an angiotensin-converting enzyme inhibitor effective for said treatment, said angiotensin-converting enzyme inhibitor having the formula I:

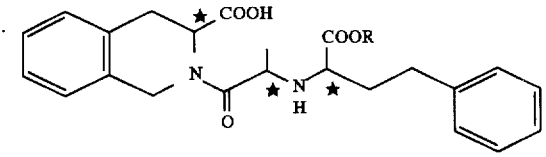

in which R is hydrogen, methyl, ethyl or benzyl; or a pharmaceutically acceptable salt thereof.

2. A method of treating cardiac insufficiency in a mammal comprising the step of administering to a mammal in recognized need of, and for the purpose of said treatment, an amount of angiotensin-converting enzyme inhibitor effective for said treatment, said angiotensin-converting enzyme inhibitor being N-(1-S-carboxy-3-phenyl-propyl)-S-alanyl-S-1,2,3,4-tetrahydroisoquinoline-3-carboxylic acid or a pharmaceutically acceptable salt thereof.

3. The method according to claim 1, wherein said inhibitor or salt thereof is administered orally or parenterally.

* * * * *